United States Patent
Kim et al.

(10) Patent No.: US 10,596,294 B2
(45) Date of Patent: Mar. 24, 2020

(54) AIR CLEANER

(71) Applicant: SEOUL VIOSYS CO., LTD., Gyeonggi-do (KR)

(72) Inventors: Jong Rack Kim, Ansan-si (KR); Jae Hak Jeong, Ansan-si (KR); Ik Hwan Ko, Ansan-si (KR); Sang Hwan Byun, Ansan-si (KR)

(73) Assignee: SEOUL VIOSYS CO., LTD., Ansan-si (KR)

( * ) Notice: Subject to any disclaimer, the term of this patent is extended or adjusted under 35 U.S.C. 154(b) by 142 days.

(21) Appl. No.: 15/531,709

(22) PCT Filed: Nov. 5, 2015

(86) PCT No.: PCT/KR2015/011868
§ 371 (c)(1),
(2) Date: May 30, 2017

(87) PCT Pub. No.: WO2016/085147
PCT Pub. Date: Jun. 2, 2016

(65) Prior Publication Data
US 2017/0348455 A1    Dec. 7, 2017

(30) Foreign Application Priority Data

Nov. 28, 2014  (KR) .......................... 10-2014-0169102
Nov. 28, 2014  (KR) .......................... 10-2014-0169103

(51) Int. Cl.
*B01D 53/00*   (2006.01)
*A61L 9/20*    (2006.01)
(Continued)

(52) U.S. Cl.
CPC .......... *A61L 9/205* (2013.01); *B01D 46/2418* (2013.01); *B01D 46/2422* (2013.01);
(Continued)

(58) Field of Classification Search
CPC ........... A61L 2209/111; A61L 2209/14; A61L 2209/212; A61L 9/205; B01D 2253/102;
(Continued)

(56) References Cited

U.S. PATENT DOCUMENTS 9,895,462 B2 *  2/2018  Law .................. F24F 13/28
2006/0201119 A1  9/2006  Song

FOREIGN PATENT DOCUMENTS

JP    H10-227499 A    8/1998
JP    H11-104225 A    4/1999
(Continued)

OTHER PUBLICATIONS

International Search Report and Written Opinion for PCT/KR2015/011868, filed Nov. 5, 2015, Applicant: Seoul Viosys Co., Ltd., dated Mar. 15, 2016, ISA/KR, 24 pages.
(Continued)

*Primary Examiner* — Sharon Pregler
(74) *Attorney, Agent, or Firm* — Perkins Coie LLP

(57) ABSTRACT

The present invention relates to an air cleaner and, more particularly, to an air cleaner provided with a housing divided into an outer housing and an inner housing, wherein the outer housing and the inner housing are separated from one another, a photocatalytic filter and a collection filter are installed in the inner housing, and air flows even through the space between the inner housing and the outer housing. The present invention provides an air cleaner comprising: an outer housing defining an inlet and an outlet; an inner housing disposed in the outer housing and formed to be separated from the outer housing; a fan installed in the inner housing to forcibly discharge air in the outlet direction; a photocatalytic filter installed in the inner housing and disposed in the direction in which air from the fan is discharged or in the direction opposite to that in which the air is
(Continued)

discharged; and an ultraviolet light source disposed upstream of the photocatalytic filter in the direction of airflow created by the fan in order to irradiate the photocatalytic filter with ultraviolet rays.

21 Claims, 11 Drawing Sheets

(51) Int. Cl.
*B01D 53/86* (2006.01)
*B01D 46/24* (2006.01)
*B01D 53/32* (2006.01)
*B01D 46/48* (2006.01)
*B01D 53/047* (2006.01)
*B01D 53/30* (2006.01)
*B01D 53/88* (2006.01)

(52) U.S. Cl.
CPC ......... *B01D 46/48* (2013.01); *B01D 53/0476* (2013.01); *B01D 53/30* (2013.01); *B01D 53/32* (2013.01); *B01D 53/86* (2013.01); *B01D 53/885* (2013.01); *A61L 2209/111* (2013.01); *A61L 2209/14* (2013.01); *A61L 2209/212* (2013.01); *B01D 2253/102* (2013.01); *B01D 2255/20707* (2013.01); *B01D 2255/802* (2013.01); *B01D 2257/93* (2013.01); *B01D 2258/06* (2013.01); *B01D 2259/4508* (2013.01); *B01D 2259/804* (2013.01)

(58) Field of Classification Search
CPC .... B01D 2255/20707; B01D 2255/802; B01D 2257/93; B01D 2258/06; B01D 2259/4508; B01D 2259/804; B01D 46/2418; B01D 46/2422; B01D 46/48; B01D 53/0476; B01D 53/30; B01D 53/32; B01D 53/86; B01D 53/885
See application file for complete search history.

(56) References Cited

FOREIGN PATENT DOCUMENTS

| JP | 2004-166918 A | 6/2004 |
|---|---|---|
| JP | 2005-143524 A | 6/2005 |
| JP | 2006-525105 A | 11/2006 |
| JP | 2015-104938 A | 6/2015 |
| JP | 2016-034602 A | 3/2016 |
| KR | 10-2004-0073857 A | 8/2004 |
| KR | 20-0439060 Y1 | 3/2008 |
| KR | 10-2008-0075290 A | 8/2008 |
| KR | 10-1191756 B1 | 10/2012 |

OTHER PUBLICATIONS

English translation of Japanese office action from corresponding Japanese Patent Application No. 2017-528532 dated Sep. 10, 2019 (7 pages).

* cited by examiner ized photocatalytic material to remove a toxic gas
AIR CLEANER

CROSS REFERENCE TO RELATED APPLICATIONS

This patent document is a 35 U.S.C. § 371 National Stage application of PCT Application No. PCT/KR2015/011868, filed on Nov. 5, 2015, which further claims the benefits and priorities of prior Korean Patent Application No. 10-2014-0169102, filed on Nov. 28, 2014, and Korean Patent Application No. 10-2014-0169103, filed on Nov. 28, 2014. The entire disclosures of the above applications are incorporated by reference in their entirety as part of this document.

TECHNICAL FIELD

The present invention relates to an air cleaner and, more particularly, to an air cleaner, which includes a housing divided into an inner housing and an outer housing separated from each other to allow air to flow through a space between the inner housing and the outer housing, and a photocatalytic filter and a collection filter disposed in the inner housing.

Furthermore, the present invention relates to an air cleaner which includes a photocatalytic filter disposed in a housing, a suction port formed on a bottom of the housing, and a base housing disposed at a lower side of the housing and supporting the housing.

BACKGROUND ART

An air cleaner is a device configured to filter dust or foreign matter from air through a filter disposed in an air flow passage while inducing forcible flow of air. A typical air cleaner is configured to collect dust through the filter and to remove a toxic gas from air in various ways.

In the air cleaner, air purification is typically performed through sequential dust collection using a pre-filter configured to filter large dust particles and a HEPA-filter configured to filter fine dust particles. This arrangement prevents such a relatively expensive HEPA filter from suffering shortened lifespan due to filtration of large dust particles.

The air cleaner may be provided with a filter for removal of a toxic gas. Among various methods for removing a toxic gas, activated carbon is generally used to remove a toxic gas from air by allowing the activated carbon to adsorb the toxic gas.

In another method, a photocatalytic material is activated through irradiation with light and air is forced to flow around the activated photocatalytic material to remove a toxic gas therefrom through photocatalytic reaction. As the photocatalytic material, titanium oxide ($TiO_2$) is generally used in the art.

When irradiated with UV light, titanium oxide is activated and causes photocatalytic reaction, and in recent years, a photocatalytic material capable of reacting in the visible range has been developed due to harmfulness of UV light and the like.

Such a photocatalytic material obtains activation energy from light. Thus, a photocatalytic material activated by UV light requires UV irradiation. Thus, upon irradiation of the photocatalytic material with UV light, a light source is necessarily separated from the photocatalytic material by a predetermined distance.

However, a typical domestic or small air cleaner has a structure in which filters are stacked to overlap each other and a fan is disposed at the rear side thereof. With such a structure, the air cleaner is restricted to a planar and flat shape. Thus, it is not easy for such an air cleaner to have a space for installation of the photocatalytic material and the light source. That is, since a typical domestic or small air cleaner generally has a planar and flat shape, a photocatalytic filter is not suitable for such an air cleaner.

Therefore, in order to apply the photocatalytic filter to such a domestic or small air cleaner, the air cleaner must be designed in consideration of an air flow passage, air suction and discharge directions, a filter installation structure, a relationship between an installation direction of filters and an air flow direction, an installation location of a light source, and the like.

In addition, in the structure wherein a UV light source and a photocatalytic filter are installed in a small air cleaner, it is necessary to adjust characteristics of UV light and the photocatalytic filter so as to secure sufficient effects of UV light and the photocatalytic filter.

On the other hand, such a typical domestic or small air cleaner is generally provided with a sensor for measuring the amount of dust in air or a toxic gas in air. However, as described above, since the domestic or small air cleaner has a flat shape and includes filters stacked to overlap each other, the air flow passage inside the housing has an insufficient space for installation of the sensor and is not suitable as a sensor installation location since air flows into the air flow passage after passing through the filter.

Conventionally, the sensor is disposed outside the housing to measure air quality. However, in this structure, since the intensity of light varies due to an illumination difference or a difference between day and night, the degree of light scattering differs even in the same amount of dust, thereby making it difficult for the sensor, which is configured to measure the amount of based on the degree of light scattering, to measure an accurate amount of dust.

Next, when the sensor for detecting toxic gases is disposed outside the housing, the sensor cannot accurately measure a toxic gas floating above air or sinking due to a lighter or heavier weight than the air, and can measure only a toxic gas present near the sensor, thereby failing to provide a suitable function of the sensor.

DISCLOSURE

Technical Problem

The present invention has been conceived to solve such problems in the related art and it is an aspect of the present invention to provide a structure allowing installation of a photocatalytic filter including a photocatalytic material and a light source within a domestic or small air cleaner, and an installation structure for a sensor capable of accurately measuring quality of interior air flowing in the air cleaner.

It is another aspect of the present invention to provide a structure of a photocatalytic filter securing very efficient performance in a compact space and a light source.

It is a further aspect of the present invention to provide an air cleaner structure that improves air flow efficiency by allowing installation of a collection filter in a compact space without increasing air flow resistance.

It is yet another aspect of the present invention to provide an air cleaner allowing easy maintenance and replacement of a filter therein.

It is yet another aspect of the present invention to provide a filter installation structure that secures optimal efficiency of a photocatalytic filter.

It is yet another aspect of the present invention to provide an air cleaner having a compact structure even with a photocatalytic filter and a light source installed therein.

It is yet another aspect of the present invention to provide a small domestic air cleaner configured to remove odors and toxic gases using a photocatalytic filter and a light source.

It is yet another aspect of the present invention to provide an air cleaner configured to improve efficiency of photocatalytic reaction through minimization of air flow resistance.

It is yet another aspect of the present invention to provide an air cleaner that is designed in consideration of an air flow direction, an installation direction of a photocatalytic filter, a shape of the photocatalytic filter, a relationship between the photocatalytic filter and a light source, and characteristics of the light source in order to improve photocatalytic reaction efficiency.

It is yet another aspect of the present invention to provide an air cleaner that allows easy maintenance and replacement of a filter despite a compact structure.

It is yet another aspect of the present invention to provide an air cleaner that includes various electric/electronic components efficiently arranged therein.

Technical Solution

In accordance with one aspect of the present invention, an air cleaner includes: a housing divided into inner and outer housings separated from each other and a sensor for measuring quality of air flowing in a separation space between the inner housing and the outer housing, and has a filter installation structure in which filters are disposed inside the inner housing and includes an enclosure type collection filter disposed upstream of an air flow, a fan is disposed downstream of the collection filter, a light source is disposed downstream of the fan, and a photocatalytic filter is disposed downstream of the light source.

More specifically, embodiments of the present invention provide an air cleaner including: an outer housing (10, 20, 40) formed with suction ports (215, 221, 222) and a discharge port (45); an inner housing (30) disposed in the outer housing and separated from the outer housing; a fan (60) disposed in the inner housing and inducing forcible discharge of air towards the discharge port; a photocatalytic filter (80) disposed in the inner housing in an air discharge direction or in an opposite direction to the air discharge direction from the fan (60); a UV light source disposed upstream of the photocatalytic filter (80) in a direction of air flow generated by the fan (60) and emitting UV light towards the photocatalytic filter; and a collection filter (70) disposed upstream of the fan, the photocatalytic filter and the UV light source in the direction of the air flow and disposed in the inner housing (30).

The air cleaner may further include a sensor (90) disposed on an outer surface of the inner housing or an inner surface of the outer housing to measure quality of air flowing in a space between the inner housing and the outer housing. Here, the sensor may be disposed between the suction port and the discharge port of the outer housing to measure the quality of air introduced through the suction ports and flowing towards the discharge port through the space between the inner housing and the outer housing.

The photocatalytic filter may be include a supporter having a plurality of cells formed as air flow passages and a photocatalytic material coated on the supporter, and an inlet of the air flow passage may be disposed towards the UV light source.

The fan (60) may flow out air in an upward direction and the photocatalytic filter may be fitted into the inner housing by being placed on the inner housing from above the inner housing. Here, the outer housing may include an upper housing (40) including an upper surface having the discharge port (45) formed thereon, and the upper housing may be detachably coupled to the outer housing such that the photocatalytic filter may be inserted into and removed from the air cleaner through an opening formed by separation of the upper housing.

The UV light source may emit UV light having a peak wavelength of 360 nm to 370 nm. The UV LED (51) may be mounted on at least one UV LED substrate (50) supported at opposite ends thereof by the inner housing and having a slim, elongated shape. A distance between the UV LED (51) and a surface of the photocatalytic filter (80) may range from 25 nm to 40 mm The collection filter (70) may include a HEPA filter (71) having a cylindrical outer peripheral surface. The collection filter (70) may further include a carbon filter (72) disposed on the outer peripheral surface of the HEPA filter (71) and having a cylindrical shape corresponding to the shape of the HEPA filter and a larger size than the HEPA filter.

The collection filter may have a cylindrical shape and include a filter member disposed on an outer peripheral surface thereof; the discharge port (45) may be formed on an upper side of the outer housing and the suction ports (215, 221, 222) may be formed at a lower portion of a side surface of the outer housing; and the collection filter may be fitted into the air cleaner in a horizontal direction such that a lower surface of the collection filter is brought into close contact with a bottom of the outer housing and an upper surface of the collection filter is brought into close contact with a lower surface of a fan installation unit (32) of the inner housing.

The outer housing may include a bottom housing (10) constituting the bottom thereof and including an upper member (11) and a lower member (12) separated a predetermined distance from each other; the lower surface of the collection filter is brought into close contact with an upper surface of the upper member (11); and a control PCB (15) controlling operation of the air cleaner and including a connector (15) connected to an exterior power source may be disposed in a space between the upper member and the lower member.

The outer housing may include a body housing (20) defining a side surface thereof, the body housing (20) may include a front housing (21) and a rear housing (22), and the rear housing is detachably coupled to the outer housing such that the collection filter may be inserted into and removed from the air cleaner through an opening formed by separation of the rear housing. The front housing (21) may be provided with a display unit (211, 212, 213) displaying an operation state of the air cleaner.

The outer housing may include an upper housing (40) defining an upper surface thereof and the upper housing (40) provided with a handling unit (41, 42, 43).

In accordance with another aspect of the present invention, an air cleaner includes: arrangement for photocatalytic reaction including a fan, a light source, and a photocatalytic filter sequentially arranged in a flow direction of air while allowing air to flow upwards in a body housing, the body housing having an air suction port formed on a bottom thereof, and a base housing disposed under the body housing to separate the body housing from a floor.

More specifically, embodiments of the present invention provide an air cleaner including: a housing (120, 130, 140) having a suction port (1231) and a discharge port (145); a fan (160) disposed in the housing and inducing forcible discharge of air towards the discharge port; a photocatalytic filter (180) disposed in the housing in an air discharge direction or in an opposite direction to the air discharge direction from the fan (160); a light source disposed upstream of the photocatalytic filter (180) in a direction of air flow generated by the fan (160) and emitting light to the photocatalytic filter; and a base housing (110) disposed at a lower side of the housing and supporting the housing such that a lower surface of the housing is separated from a floor.

The photocatalytic filter may be include a supporter having a plurality of cells formed as air flow passages and a photocatalytic material coated on the supporter and having an air flow passage formed therebetween, and an inlet of the air flow passage may be disposed towards the light source.

The housing (120, 130, 140) may include: an outer housing (120, 140) having the suction port (1231) formed on a bottom surface thereof and the discharge port (145) formed on an upper surface thereof; and an inner housing (130) in which the fan (160), the light source, and the photocatalytic filter (180) are disposed.

The fan (160) may flow out air in an upward direction and the photocatalytic filter may be fitted into the inner housing by being placed on the inner housing from above the inner housing.

The outer housing may include an upper housing (140) including an upper surface having the discharge port (45) formed thereon, and the upper housing may be detachably coupled to the outer housing such that the photocatalytic filter can be inserted into and removed from the air cleaner through an opening formed by separation of the upper housing.

The UV light source may include a UV LED (151) emitting UV light having a peak wavelength of 360 nm to 370 nm.

The UV LED (151) may be mounted on at least one UV LED substrate (150) supported at opposite ends thereof by the housing and having a slim, elongated shape.

The base housing (110) may include: a neck member (111) connected to a central portion of a lower side of the housing and having a width gradually increasing towards a lower end thereof; and a lower member (112) formed at the lower side of the neck member, in which the neck member (111) is communicated with an interior space of the housing through an upper side thereof; and a control PCB (113) controlling operation of the air cleaner and including a connector (15) connected to an exterior power source may be disposed in a space between the neck member and the lower member.

The housing may include a side housing (121) defining a side surface thereof and provided with a display unit (1211, 1212, 1213) displaying an operation state of the air cleaner.

The base housing (110) may include a neck member (111) connected to a central portion of a lower side of the housing and having a width gradually increasing towards a lower end thereof, and a lower housing (123) constituting a lower portion thereof, in which an upper end of the neck member (111) is secured to a central portion of the lower housing (123) and the suction port (1231) may be formed along an outer circumference of the central portion of the lower housing (123).

The lower housing (123) may include a plurality of ribs (1232) radially extending from the central portion thereof to an outer periphery thereof and a grate (1233) formed between the plurality of ribs.

The housing (120, 130, 140) may include: an outer housing (120, 140) having the suction port (1231) and the discharge port (145) formed thereon; and an inner housing (130) which receives the fan (160), the light source, and the photocatalytic filter (180) therein, in which the outer housing (120, 140) includes a side housing (121) defining a side surface thereof and having a mounting unit (125) of the inner housing inwardly protruding along an inner surface of a lower end the side housing (121).

The inner housing may include: a fan housing (132) receiving the fan (160) therein and a photocatalyst housing (133) receiving the photocatalytic filter (180) and the light source therein, in which the fan housing may be disposed on the mounting unit and the photocatalyst housing may be disposed on the fan housing.

The housing may include an upper housing (40) defining an upper surface thereof, and the upper housing (40) provided with a handling unit (141, 142, 143).

Advantageous Effects

According to the present invention, the air cleaner can remove a toxic gas from air using a photocatalytic filter and a light source therein while maintaining a compact structure.

According to the present invention, despite having a small structure, the air cleaner has high purification efficiency by reducing resistance to an air flow generated by a filter.

According to the present invention, despite a compact structure, the air cleaner can secure high efficiency in removal of a toxic gas using the photocatalytic filter and the light source disposed therein.

According to the present invention, the air cleaner allows convenient maintenance and repair.

According to the present invention, despite having a small structure, the air cleaner allows an air flow in a linear direction so as to reduce resistance to the air flow, thereby improving air purification efficiency.

The above and other effects of the present invention will become apparent from the detailed description of the present invention.

MODE FOR INVENTION

Hereinafter, exemplary embodiments of the present invention will be described in detail with reference to the accompanying drawings.

The present invention is not limited to the following embodiments and may be embodied in different ways. Rather, the following embodiments are given by way of illustration only to provide thorough understanding of the invention to those skilled in the art.

Figure 1:
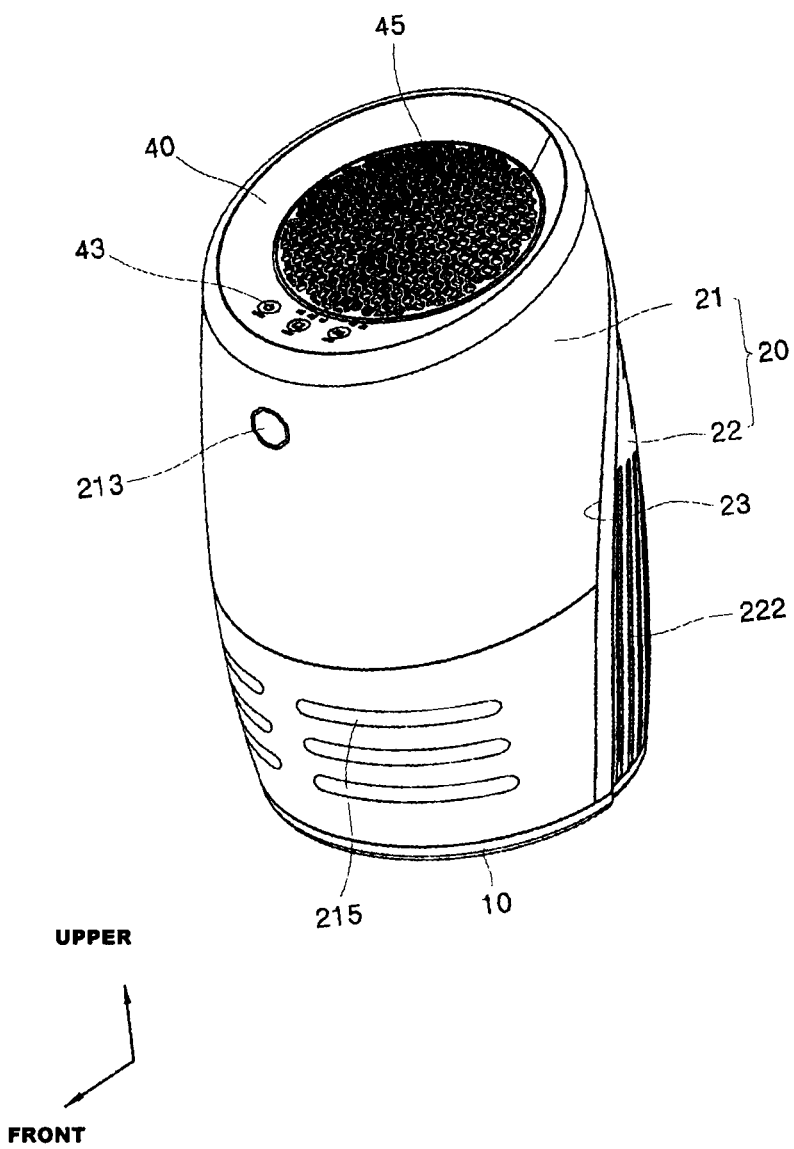
FIG. 1 is a perspective view of an air cleaner according to one embodiment of the present invention.
Figure 2:
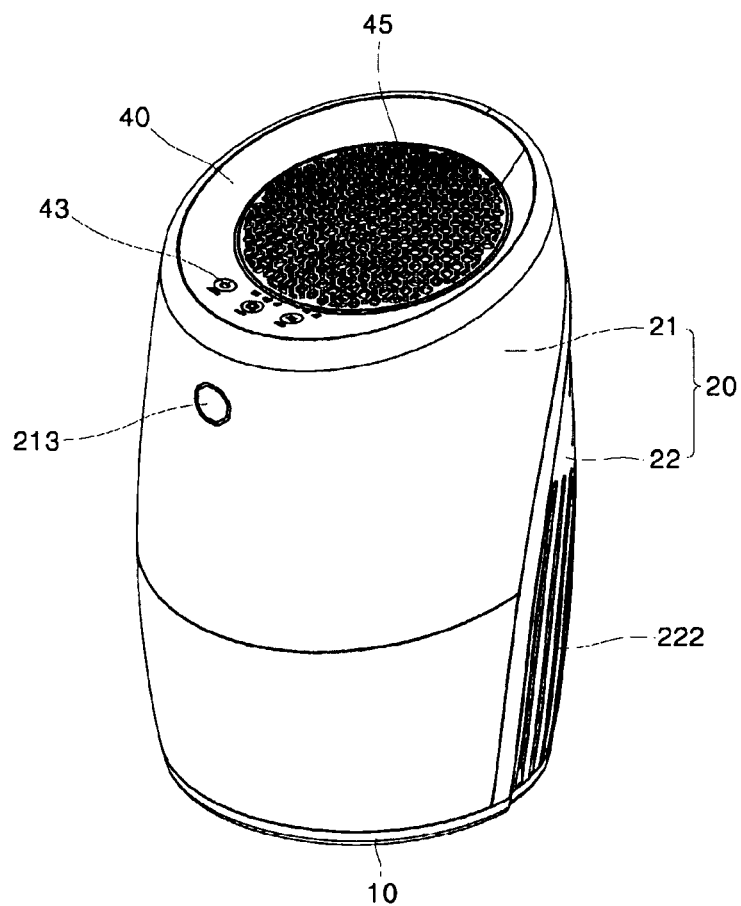
FIG. 2 is a perspective view of an air cleaner according to another embodiment of the present invention.
Figure 3:
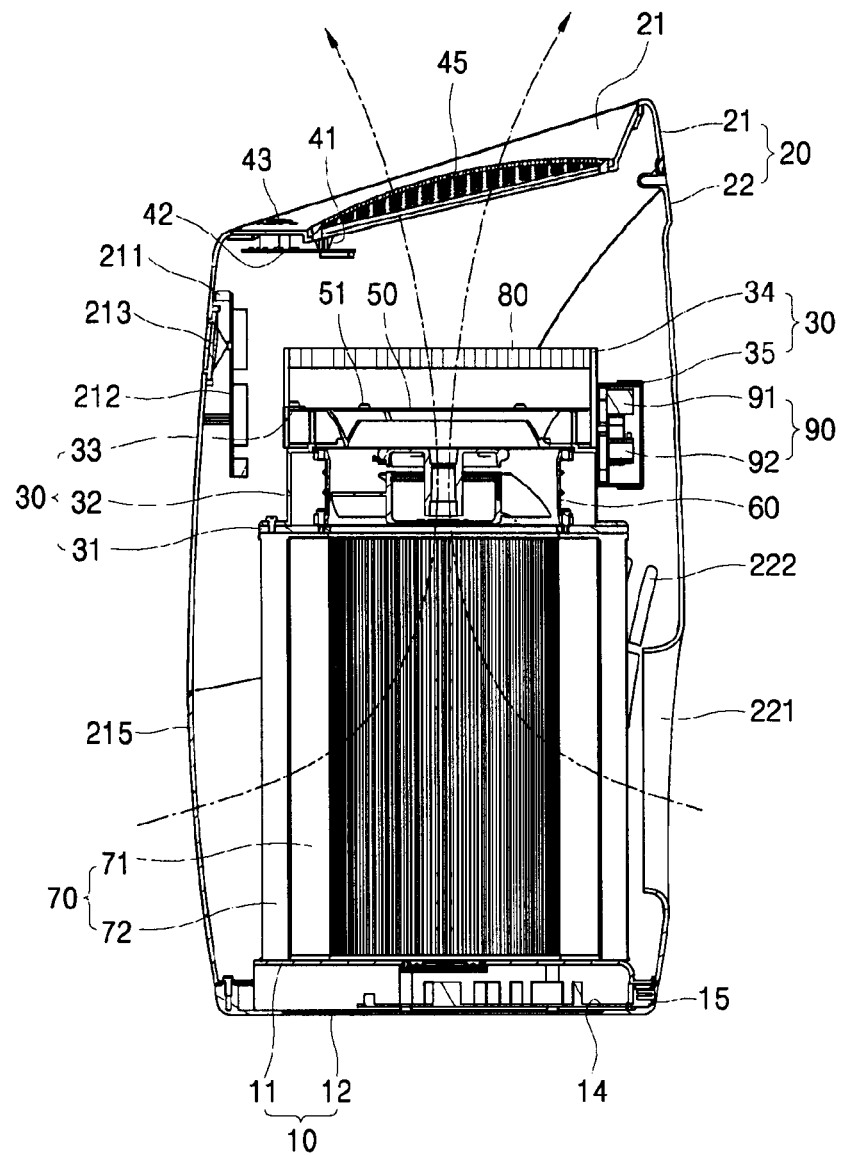
FIG. 3 is a side sectional view of the air cleaner according to the embodiment of the present invention.
Figure 4:
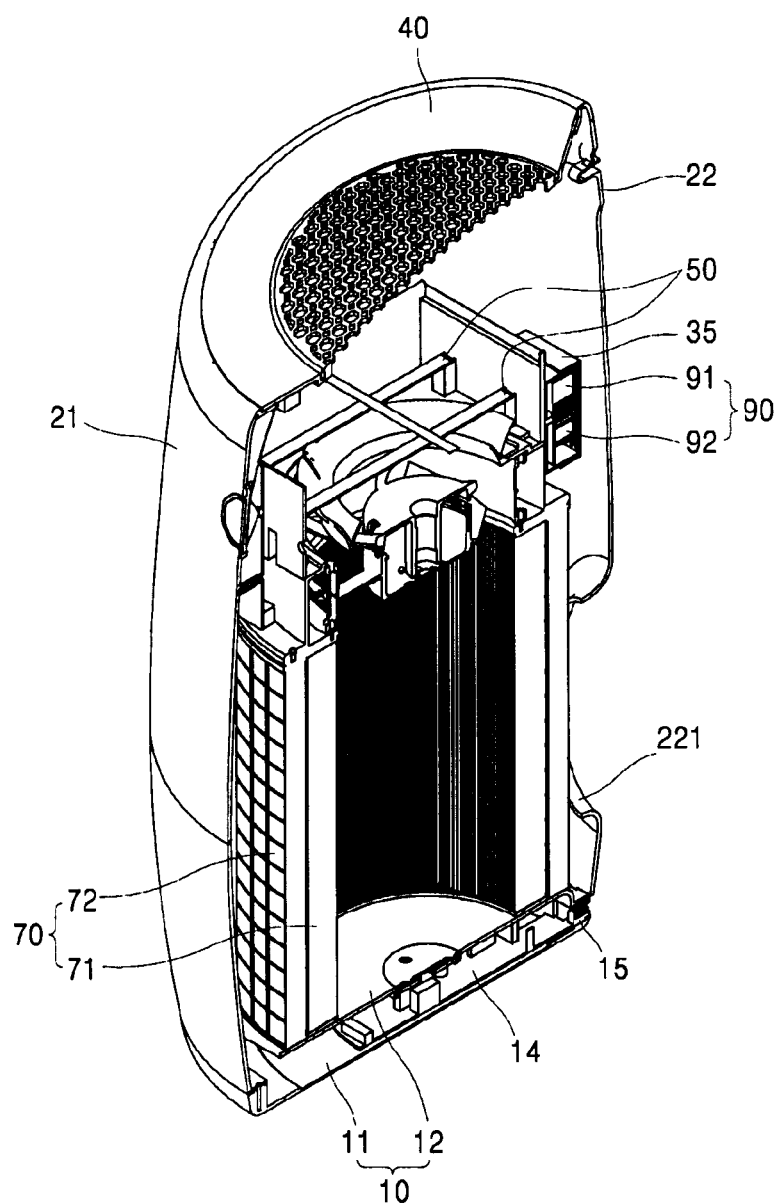
FIG. 4 is a perspective view of the air cleaner shown in FIG. 3, from which a photocatalytic filter is removed.
Figure 5:
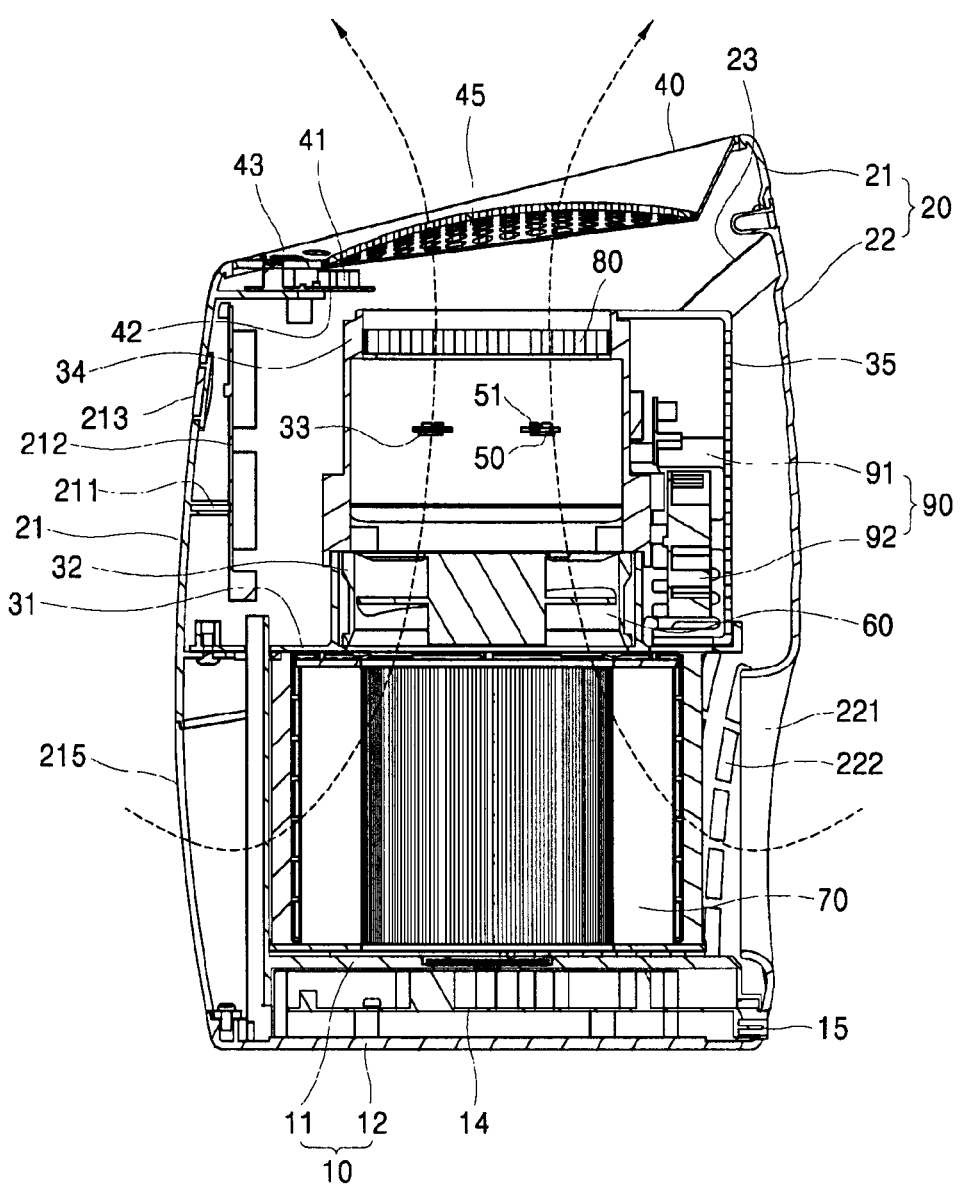
FIG. 5 is a side sectional view of the air cleaner according to the one embodiment of the present invention, which has a smaller structure than the air cleaner of FIG. 3.
Figure 6:
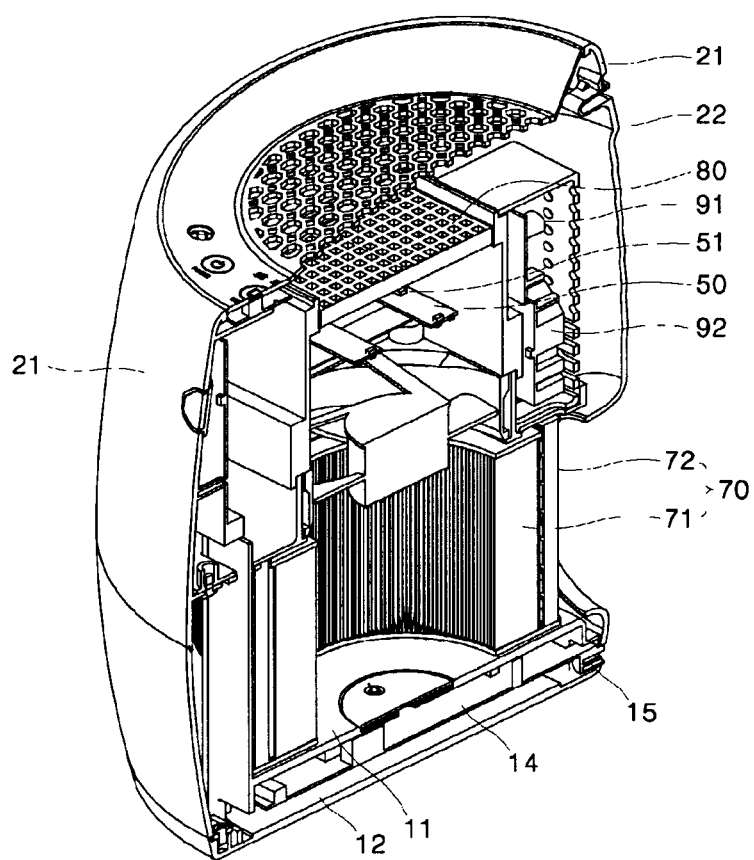
FIG. 6 is a perspective view of the air cleaner shown in FIG. 5.

FIG. 1 is a perspective view of an air cleaner according to one embodiment of the present invention, having a structure wherein air suction ports are formed at front and rear sides thereof, FIG. 2 is a perspective view of an air cleaner according to another embodiment of the present invention, having a structure wherein an air suction port is formed at a rear side thereof, FIG. 3 is a side sectional view of the air cleaner shown in FIG. 1, FIG. 4 is a perspective view of the air cleaner shown in FIG. 2, from which a photocatalytic filter is removed, FIG. 5 is a side sectional view of another embodiment of the air cleaner shown in FIG. 1, which has a smaller structure than the air cleaner of FIG. 3, and FIG. 6 is a perspective view of another embodiment of the air cleaner shown in FIG. 2, which has a smaller structure than the air cleaner of FIG. 4.

The air cleaners shown in FIG. 1, FIG. 3 and FIG. 5 have a structure wherein air suction ports are formed at front and rear sides thereof, and the air cleaners shown in FIG. 2, FIG. 4 and FIG. 6 have a structure wherein an air suction port is formed at the rear side thereof.

The air cleaners of FIG. 5 and FIG. 6 have a smaller size than the air cleaners of FIG. 3 and FIG. 4.

First, referring to FIG. 1 and FIG. 2, the air cleaner according to embodiments of the present invention will be described. The air cleaner according to the embodiments of the invention includes an outer housing 10, 20, 40 having a substantially cylindrical structure. The outer housing includes an upper housing 40 defining an upper surface of the air cleaner, a body housing 20 defining a side surface thereof the air cleaner, and a bottom housing 10 defining a bottom thereof.

The upper housing 40 has a discharge port 45 formed at an upper side thereof. The discharge port has a grate shape to block foreign matter from entering the upper housing therethrough. The upper housing is provided at a front region thereof with a button 43. Accordingly, operation of the air cleaner can be controlled through the button by a user. The button may be a physical button or a touch type button. With the structure wherein the button is disposed on the upper side of the air cleaner, it is possible to prevent movement of the air cleaner by force applied thereto when a user pushes the button. In a structure wherein the button is disposed on a front side of the air cleaner, there is a problem in that the air cleaner is pushed backwards whenever a user pushes the button. The structure of the air cleaner having the button disposed on the upper side thereof can prevent such a problem.

Next, a display screen 213 for supplying information regarding operation of the air cleaner is formed on a front side of the body housing 20. The display screen disposed on the front side of the body housing can provide better visibility than the structure wherein the display screen is disposed on the upper side of the air cleaner. The body housing 20 is divided into a front housing 21 disposed at a front side with reference to a boundary 23 and a rear housing 22 disposed at a rear side with reference to the boundary 23. As shown in the drawings, the front housing 21 is fastened at an upper side thereof to the upper housing 40, at a rear side thereof to the rear housing 22, and at a lower side thereof to the bottom housing 10. The rear housing 22 is fastened at a front side thereof to the front housing 21 and at a lower side thereof to the bottom housing 10. As described below, the upper housing 40 is detachably fastened to the front housing 21 and the rear housing 22 is also detachably fastened to the front housing 21.

FIG. 1 shows the air cleaner in which both the front housing 21 and the rear housing 22 are formed with suction ports 215, 222, and FIG. 2 shows the air cleaner in which only the rear housing 22 is formed with the suction port 222. All of these air suction ports are formed at a lower portion of the body housing 20. Thus, in the structure of the air cleaner according to the present invention, air is suctioned through the suction ports 215, 221, 222 formed at the lower portion of the body housing and is then discharged upwards through the discharge port 45. Since dust generally sinks, it is desirable that the suction ports be formed at the lower portion of the air cleaner. In addition, the discharge port is formed to face upwards, thereby preventing flow of purified air from lifting dust on the floor of a room.

Next, the inner structure of the air cleaner according to these embodiments of the invention will be described with reference to FIG. 3 to FIG. 6. The inner housing 30 is disposed in the interior space of the outer housing to be separated from the outer housing. The inner housing 30 is provided with filters 70, 80 and light sources 50, 51.

First, the inner housing 30 is provided at a lower side thereof with a cylindrical collection filter 70. The collection filter 70 is open at upper and lower sides thereof and has a side surface surrounded by a filter member, and is disposed under the inner housing 30. An upper surface of the collection filter 70 closely contacts a lower surface of the inner housing and a lower surface of the collection filter closely contacts an upper surface of the bottom housing 10. In this structure, air can flow into the inner housing only after passing through the filter member of the collection filter 70. As described above, since the suction ports 215, 221, 222 are provided to the outer housing, the inner and outer housings are separated from each other, and the inner housing is provided at the lower side thereof with the collection filter 70, as shown in the drawings, external air is introduced into the outer housing through the suction ports 215, 221, 222, passes a space between the inner housing and the outer housing, and then flows into the inner housing through the collection filter. Since the collection filter has a cylindrical shape, the collection filter has a much larger area than a planar collection filter. Accordingly, as compared with the planar collection filter, the cylindrical collection filter has relatively small flow resistance to air passing through the collection filter. In addition, according to the present invention, since there is a space between the inner housing and the outer housing, air can evenly pass through the collection filter.

The collection filter 70 includes a HEPA filter 71 formed on a cylindrical outer peripheral surface thereof and a carbon filter 72 surrounding an outer surface of the HEPA filter 71. That is, the carbon filter 72 is disposed on an outer surface of the HEPA filter 71. These filters are detachably fastened to each other and thus can be replaced by new ones, as needed. Separation of these filters may be performed by moving these filters in upward and downward directions, as shown in the drawings, or by fastening a belt type carbon filter around the outer surface of the cylindrical HEPA filter similar to how a lap belt is worn.

The collection filter 70 may be removed from the air cleaner through an opening formed by separation of the rear housing 22. That is, the collection filter may be provided to the inner housing in a direction from the rear side to the front side, and may be separated therefrom in a direction from the front side to the rear side.

The carbon filter 72 surrounding the collection filter 70 includes activated carbon particles received in a case having a sieve shape to prevent leakage of the activated carbon particles. The sieve-shaped case can prevent leakage of the activated carbon particles while filtering relatively large dust particles. Activated carbon adsorbs toxic gas present in air. Particularly, activated carbon adsorbs ammonia or acetic acid to allow acetaldehyde, which reacts more slowly than these toxic gases in photocatalytic reaction, to decompose faster than these toxic gases in a photocatalytic filter described below.

The HEPA filter 71 serves to filter out fine dust from air flowing into the inner housing. As such, in the air cleaner according to the present invention, fine dust is first filtered through the HEPA filter, thereby preventing accumulation of dust on the fan 60 or the photocatalytic filter 80 disposed at the rear of the collection filter and on the light sources 50, 51.

In the inner housing 30, an accommodation unit 31 configured to receive the collection filter therein is provided at an upper side thereof with a fan mounting unit 32. The fan 60 is mounted on the fan mounting unit 32 and generates a flow of air in the upward direction. Upon rotation of the fan 60, a negative pressure is generated in the upward direction within the collection filter 70 such that air outside the collection filter can be introduced into the collection filter having a relatively low pressure and can be compressed and lifted in the upward direction by the fan. According to the present invention, since the fan is disposed at the rear of the filter resisting the air flow, a pressure difference occurs between the interior space of the collection filter and an exterior space thereof to cause air flow, thereby improving filter passage efficiency of air.

A substrate mounting unit 33 for a UV LED substrate 50 is disposed on an upper side of the fan mounting unit 32, and a photocatalytic filter mounting unit 34 having the photocatalytic filter 80 mounted thereon is disposed above the substrate mounting unit 33 to be separated therefrom by a predetermined distance.

The UV LED substrate 50 mounted on the substrate mounting unit 33 has a slim, elongated plate shape and includes a UV LED 51 mounted on an upper surface thereof. The UV LED substrate may be provided in plural depending upon the number of UV LEDs corresponding to the size of the air cleaner. The air cleaner shown in FIG. 3 and FIG. 4 includes four substrates and the air cleaner shown in FIG. 5 and FIG. 6 includes two substrates. Although not shown in the drawings, a lower surface of the UV LED substrate 50 preferably has a streamline-shaped air induction structure having a downwardly convex cross-section to prevent increase in resistance to the air flow due to the flat shape of the substrate.

UV light emitted from the UV LED generally has a spreading angle of about 120° and is emitted towards the photocatalytic filter 80. The photocatalytic filter 80 has a structure wherein a photocatalytic material is secured to a supporter. In some embodiments, titanium oxide may be used as the photocatalytic material.

The photocatalytic filter has a maximum UV absorption rate near a wavelength of 270 nm and has a UV absorption rate linearly decreasing towards a wavelength of 400 nm. Thus, it can be considered that a UV LED having a peak wavelength of 270 nm is advantageous. However, in practical use of the UV LED, it could be ascertained that a UV LED having a peak wavelength of 365 nm provides the most efficient photocatalytic activation. It can be ascertained that this phenomenon results from luminous efficacy of the UV LED. That is, since luminous intensity of the UV LED rapidly decreases with decreasing peak wavelength, it could be ascertained that the UV LED having a peak wavelength of 365 nm provides most efficient photocatalytic reaction in practice.

In other words, since the UV LED having a peak wavelength of about 270 nm has a low intensity of UV light, the intensity of UV light emitted from the UV LED is not sufficient for the surface of the photocatalytic filter, thereby providing insufficient photocatalytic reaction. Thus, the intensity of UV light can be increased by increasing the number of UV LEDs. However, since this structure can obstruct the flow of air, there is a limitation in increase in size of the substrate, and manufacturing costs and power consumption are also rapidly increased with increasing number of UV LEDs.

As a result of experimentation by taking this fact into account, it could be ascertained that a UV LED having a peak wavelength of 340 nm or less provides rapid deterioration in efficiency of removing odors through the photocatalytic filter.

In addition, when a UV LED having a peak wavelength of 380 nm or more was used, there was no significant difference between the UV LED and a black light as a typical lamp due to significant deterioration in UV absorption rate of the photo-catalyzer, and this result meant that there the effects of the UV LED became insignificant.

As a result of experimentation, it could be ascertained that a UV LED having a peak wavelength of 360 nm to 370 nm provides the maximum performance in removal of odors through the photocatalytic filter.

The photocatalytic filter has a structure wherein a photocatalytic material is coated onto a supporter composed of a plurality of cells disposed adjacent to each other and having an air flow passage formed therebetween and having a regular hexagonal cross-section or a square cross-section like a honeycomb shape, in which an inlet of the air flow passage is disposed in a vertical direction, that is, towards the UV light source, as shown in FIG. 3. With such a structure, the photocatalytic filter allows UV light to reach not only an outer surface of the photocatalytic filter but also an inner surface of the air flow passage, thereby further promoting photocatalytic activation.

A distance between the UV LED 51 and a front side of the photocatalytic filter 80 facing the UV LED 51 differs depending upon variation in flow characteristics of air and the intensity and irradiation area of UV light reaching the photo catalytic filter, which depend on the distance between the UV LED substrate and the photocatalytic filter. As a result of experimentation, it could be ascertained that, when the distance between the UV LED and the front side of photocatalytic filter is 2.5 cm or less or 4 cm or more, the air cleaner suffered from significant deterioration in efficiency in removal of odors.

If the distance between the UV LED and the front side of photocatalytic filter is 2.5 cm or less, the area of the photocatalytic filter irradiated with UV light is reduced and photocatalytic activation efficiency is not further improved even with increase in the intensity of UV light per unit area of the photocatalytic filter. Furthermore, if the UV LED substrate is disposed too close to the photocatalytic filter, the air flow becomes inefficient in the middle region of the photocatalytic filter mainly exposed to UV light, causing reduction in the amount of air contacting a region of the photocatalytic filter in which the most efficient photocatalytic activation occurs and finally deterioration in efficiency of removal of odors through the photocatalytic filter. If the distance between the UV LED and the front side of photocatalytic filter is 4 cm or more, the intensity of UV light per unit area of the photocatalytic filter is reduced, causing deterioration in photocatalytic activation efficiency.

On the other hand, the flow direction of air must be taken into account. According to the present invention, the flow direction of air is the same as the direction of the UV LED, that is, the UV light source, facing the photocatalytic filter.

This feature is obtained based on an experimentation result. That is, it could be ascertained that, when the air flow direction is set in the same direction as the direction from the UV light source towards the photocatalytic filter, the air cleaner provides better purification efficiency than when the air flow direction is opposite the direction from the UV light source towards the photocatalytic filter.

Since the photocatalytic filter has a structure allowing air to pass through the plurality of air flow passages, air pressure decreases due to flow resistance while the air passes through the photocatalytic filter. On the other hand, photocatalytic reaction becomes more active with increasing contact area between the surface of the photocatalytic material and the air. Accordingly, the structure allowing decomposition of a toxic gas in the air through contact with the photocatalytic material before the air undergoes pressure drop while passing through the photocatalytic filter provides higher decomposition efficiency than the structure allowing decomposition of a toxic gas in the air through contact with the photocatalytic material after the air passes through the photocatalytic filter and undergoes pressure drop. Accordingly, the air cleaner according to the present invention is configured to allow air to flow in the direction from the UV light source towards the photocatalytic filter, thereby further improving air purification efficiency of the photocatalytic filter.

Next, as shown in the drawings, in the inner housing, a lower end of the photocatalytic filter mounting unit 34 has a step shape. Accordingly, the photocatalytic filter 80 may be mounted on the photocatalytic filter mounting unit 34 by placing the photocatalytic filter 80 thereon from above the inner housing.

On the other hand, in the outer housing, the upper housing 40 may be detachably coupled to the body housing 20, more specifically to an upper surface of the front housing 21. Accordingly, when the upper housing 40 is separated from the body housing 20, an opening is formed at an upper portion of the body housing 20 such that the photocatalytic filter can be inserted into or removed from the body housing 20 therethrough.

A slight space is present between an upper end of the inner housing and an upper end of the outer housing and air flows in the upward direction in this space, as shown in the drawings. Such air flow also lifts air present in the space between the inner housing and the outer housing.

According to the present invention, sensors 90 for measuring the quality of air are disposed in the space between the inner housing and the outer housing instead of being disposed outside the outer housing. Although a dust sensor 91 and a gas sensor 92 are illustrated as being disposed on the outer surface of the inner housing 30 in the embodiments shown in the drawings, it should be understood that these sensors may be disposed on the inner surface of the outer housing. For convenience of wiring, the sensors are preferably disposed on the inner surface of the front housing rather than the rear housing, more preferably on the outer surface of the inner housing.

The space between the inner housing and the outer housing is filled with air having the same degree of contamination as external air not having passed through the filter. That is, since the outer housing has a continuous flow of air, which is calmer than the air flow passing through the inner housing and continues from the suction ports to the discharge port, air having the same degree of contamination as external air continues to flow in the space, which is isolated from an external environment, thereby enabling more accurate measurement of the degree of contamination through measurement of the quality of air in the space.

According to the present invention, electric/electronic components are very efficiently arranged in the air cleaner. According to the present invention, the bottom housing 10 includes an upper member 11 and a lower member 12 separated a predetermined distance from each other. Thus, a space is formed between the upper and lower members and is provided with a control PCB 14 for controlling operation of the air cleaner. That is, the control PCB 14 is disposed on the bottom of the air cleaner to be embedded in the space between the upper member and the lower member such that the control PCB 14 is not exposed even when the rear housing 22 is detached for maintenance or repair of the air cleaner. A connector 15 is disposed at a rear side of the control PCB and is connected to an external power source.

Power supplied through the connector is supplied to the fan 60, the UV LED substrate 50, and the sensors 90 in the inner housing. In addition, the power source is connected to a display unit 211, 212, 213 mounted on the front housing 21 and a handling unit 41, 42, 43 mounted on the upper housing 40.

The display unit includes a fastening portion 211 formed on an inner surface of the front housing 21, a display PCB 212 fastened to the fastening portion 211, and a display screen 213 disposed on the front housing to be adjacent to the display PCB to display operation of the air cleaner through on/off and colors of a light emitting diode provided to the display PCB.

The handling unit is disposed near the display unit, and includes a fastening portion 41 formed on a lower surface of the upper housing 40, a handling PCB 42 fastened to the fastening portion 41, and the button 43 disposed on the front region of the upper housing 40.

Accordingly, power lines connected to the two PCBs 212, 42 can be disposed along the inner surface of the front housing.

Figure 7:
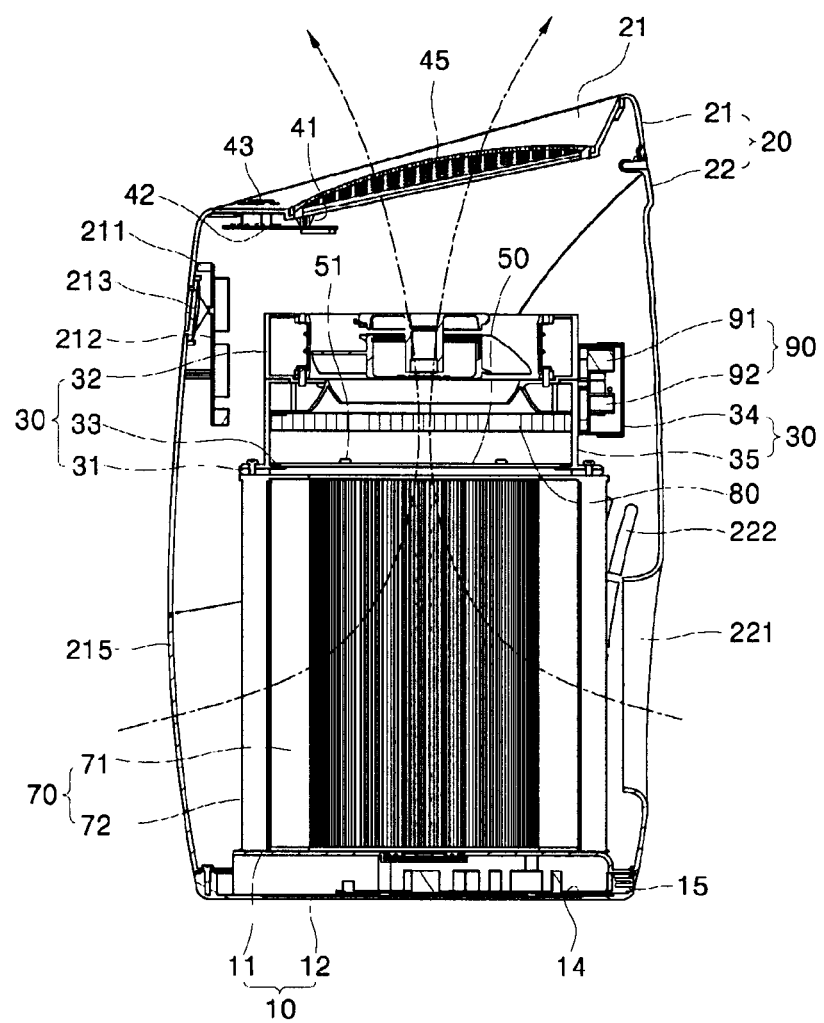
FIG. 7 is a side sectional view of another embodiment of the air cleaner shown in FIG. 3.

FIG. 7 is a side sectional view of another embodiment of the air cleaner shown in FIG. 3. The air cleaner of FIG. 7 has substantially the same structure as the air cleaner of FIG. 3 except that the fan mounting unit 32 is disposed above the UV LED substrate mounting unit 33 and the photocatalytic filter mounting unit 34 in the inner housing 30. The following description will focus on different features of the air cleaner according to this embodiment and repeated description of the same components will be omitted.

That is, referring to FIG. 7, in the inner housing 30, the substrate mounting unit 33 for the UV LED substrate 50 is disposed on the accommodation unit 31, which receives the collection filter, and the photocatalytic filter mounting unit 34, on which the photocatalytic filter 80 is mounted, is separated above the substrate mounting unit 33 by a predetermined distance. The UV LED substrate 50 mounted on the substrate mounting unit 33 has a slim, elongated plate shape and includes a UV LED 51 mounted on an upper surface thereof. The substrate may be provided in plural depending upon the number of UV LEDs corresponding to the size of the air cleaner.

The fan mounting unit 32 is disposed above the substrate mounting unit 33 for the UV LED substrate 50. The fan 60 mounted on the fan mounting unit 32 generates a flow of air flowing in the upward direction. Upon rotation of the fan 60, a negative pressure is generated in the upward direction within the collection filter 70, whereby air outside the collection filter flows into the interior space of the collection filter having a relatively low pressure, is compressed and lifted by the fan. According to this embodiment of the invention, since the fan is disposed at the rear of the filter, which resists the flow of air, a pressure difference is generated between the interior space of the collection filter and an external space by operation of the fan and induces an air flow, thereby improving efficiency in passage of air through the filter.

The air flow generated by the pressure difference passes through the photocatalytic filter below the fan 60 to allow purification of air and is discharged through the discharge port 45 via the fan.

As compared with the air cleaner of FIG. 3, since the direction of the air flow is the same, there is no significant difference in air purification efficiency, and since the UV LED 51 is disposed more deeply inside the air cleaner, it is possible to reduce a danger of UV exposure through the discharge port 45. In addition, the structure of the air cleaner according to this embodiment facilitates separation of the photocatalytic filter through an opening formed by separation of the rear housing 22 upon cleaning or replacement.

Figure 8:
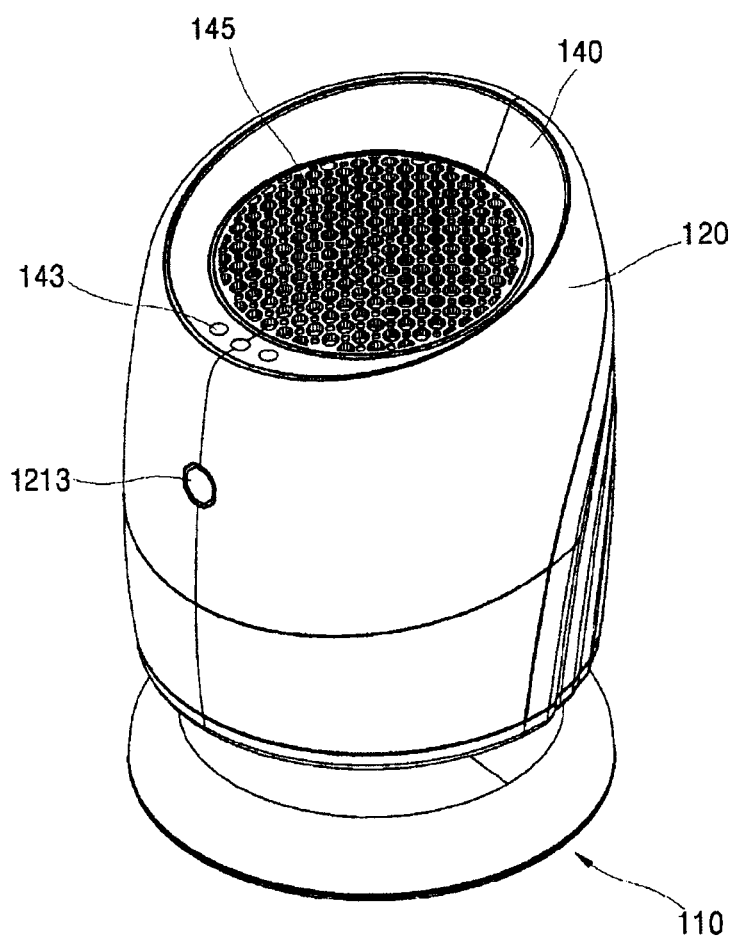
FIG. 8 is a perspective view of an air cleaner according to a further embodiment of the present invention.
Figure 9:
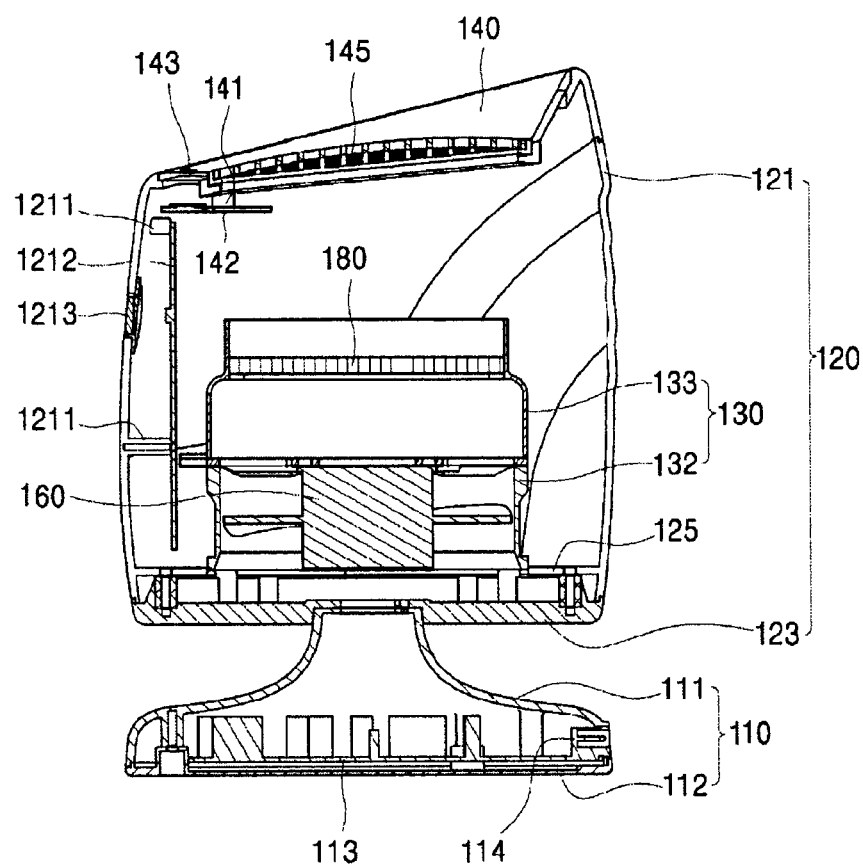
FIG. 9 is a side sectional view of the air cleaner shown in FIG. 8.
Figure 10:
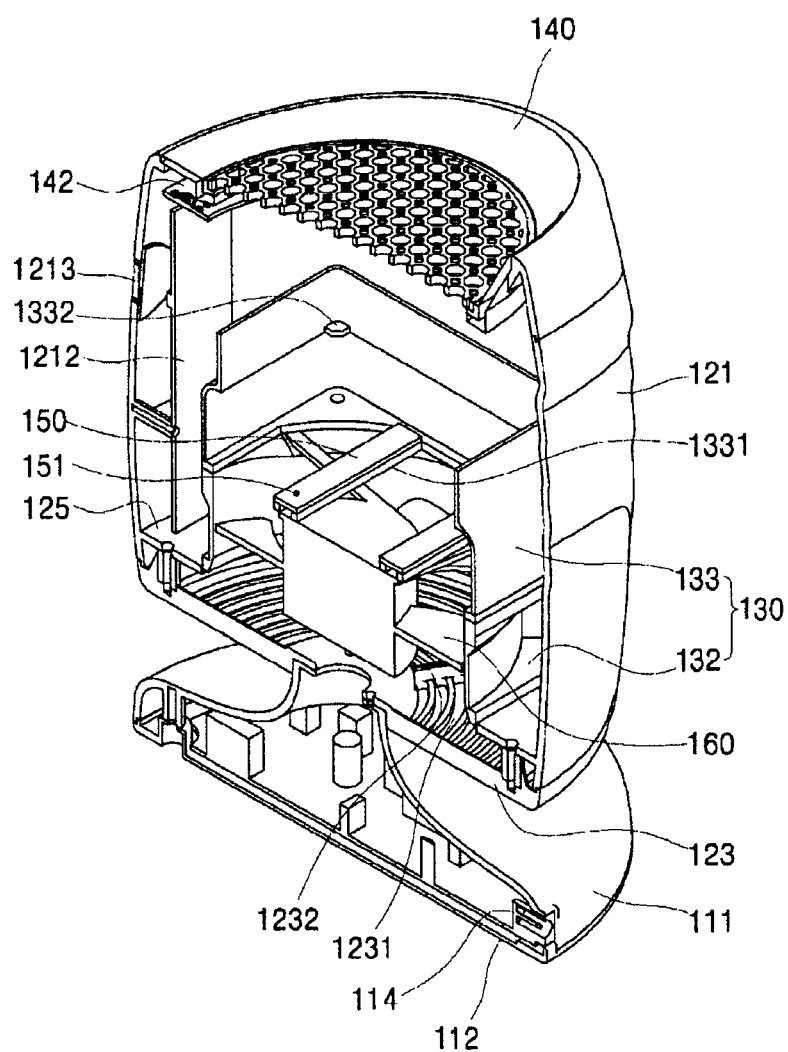
FIG. 10 and FIG. 11 are a front perspective view and a rear perspective view of the air cleaner shown in FIG. 9, respectively.
Figure 11:
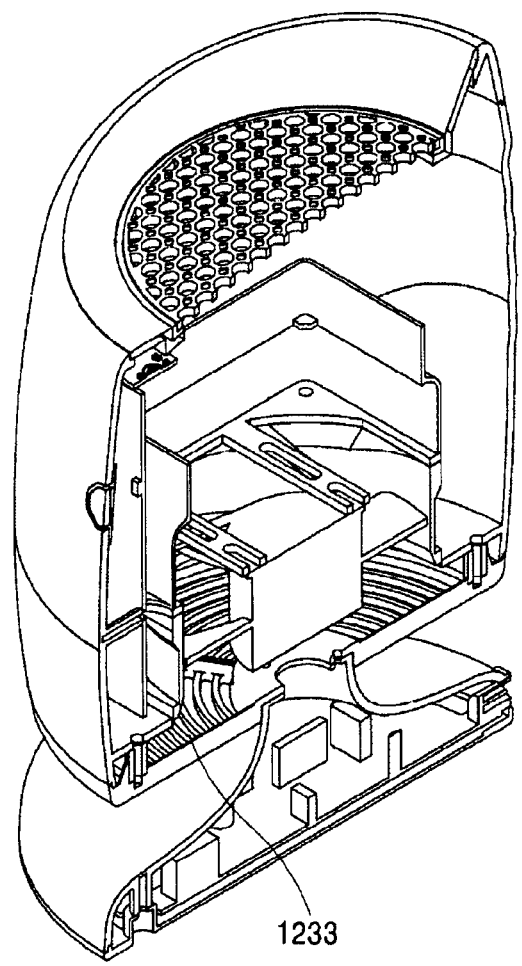

FIG. 8 is a perspective view of an air cleaner according to a further embodiment of the present invention, FIG. 9 is a side sectional view of the air cleaner shown in FIG. 8, and FIG. 10 and FIG. 11 are a front perspective view and a rear perspective view of the air cleaner shown in FIG. 9, respectively.

First, an air cleaner according to this embodiment of the invention will be described with reference to FIG. 8. The air cleaner includes an outer housing 120, 140 having a substantially cylindrical shape and a base housing 110 acting as a leg supporting the outer housing 120, 140. The base housing 110 is configured to support a central portion of a lower surface of the outer housing 120, 140 such that the lower surface of the outer housing can be exposed to air. The outer housing 120, 140 includes an upper housing 140 defining an upper surface of the air cleaner and a body housing 120 defining a body of the air cleaner.

The upper housing 140 has a discharge port 145 formed at an upper side thereof. The discharge port has a grate shape to block foreign matter from entering the upper housing therethrough. The upper housing is provided at a front region thereof with a button 43. Accordingly, operation of the air cleaner can be controlled through the button by a user. The button may be a physical button or a touch type button. With the structure wherein the button is disposed at an upper side of the air cleaner, it is possible to prevent movement of the air cleaner by force applied thereto when a user pushes the button. In a structure wherein the button is disposed on a front side of the air cleaner, there is a problem in that the air cleaner is pushed backwards whenever a user pushes the button. The structure of the air cleaner having the button disposed at the upper side thereof can prevent such a problem.

Next, a display screen 1213 for supplying information regarding operation of the air cleaner is formed on a front side of the body housing 120. The display screen disposed on the front side of the body housing can provide better visibility than the structure wherein the display screen is disposed on the upper side of the air cleaner. The body housing 120 is divided into a side housing 121 defining a side surface of the body of the air cleaner and a lower housing 123 defining a bottom of the body of the air cleaner. As shown in the drawings, the side housing 121 is fastened at an upper side thereof to the upper housing 40 and at a lower side thereof to the lower housing 123. The lower housing 123 is fastened at a lower side thereof to a base housing 110. As described below, the upper housing 140 is detachably fastened to the side housing 121.

Although not shown in FIG. 8, referring to FIG. 10 and FIG. 11, a suction port 1231 is formed on the lower housing 123 defining the bottom of the outer housing. Accordingly, in the structure of the air cleaner according to this embodiment, air is suctioned through the suction port 1231 disposed on the bottom of the air cleaner to flow upwards, and is then discharged upwards through the discharge port 145.

In this embodiment, the discharge port is disposed to face upwards, thereby preventing a flow of purified air from lifting dust on the floor of a room. In addition, since a user can suffer from an unpleasant feeling when directly exposed to the flow of purified air discharged through a side surface of the air cleaner, it is desirable that discharge port be disposed to face upwards.

In the structure wherein the discharge port is disposed to face upwards, it is advantageous in reduction of flow loss of air that the air flow be generally directed upwards in the air cleaner. However, since a typical air cleaner has a body disposed to adjoin the floor of a room and a suction port formed on a side surface thereof, a curved air flow is generated in the air cleaner, thereby causing significant flow loss.

In the air cleaner according to this embodiment, the bottom surface of the outer housing 120, 140 is supported by the base housing 110 to be separated from the floor and the suction port 1231 is provided to the bottom surface of the outer housing 120, 140 such that air generally flows in the upward direction within the air cleaner. Not only does this structure provide an efficient flow of the air, but also further improves photocatalytic reaction efficiency of the photocatalytic filter described below.

Next, the inner structure of the air cleaner according to this embodiment will be described with reference to FIG. 9 to FIG. 11. An inner housing 130 is disposed in the interior space of the outer housing 120, 140 and receives a photocatalytic filter 180, a UV LED substrate 150 and a fan 160. That is, the inner housing acts as a housing for receiving interior components of the air cleaner.

The air cleaner according to this embodiment includes a mounting unit 125 which inwardly protrudes from an inner surface of a lower portion of the side housing 121. The inner housing is mounted on the mounting unit. The inner housing includes a fan housing 132 that receives the fan 160, and a photocatalyst housing 133 that receives the photocatalytic filter and the UV LED substrate, in which the fan housing 132 is disposed on the mounting unit 125 and the photocatalyst housing is disposed on the fan housing 132. Thus, in the inner housing, the fan 160, the UV LED 150 and the photocatalytic filter 180 are sequentially disposed from the bottom of the inner housing.

The fan 160 received in the fan housing 132 generates a flow of air in the upward direction. Accordingly, air outside the air cleaner is introduced into the air cleaner through the suction port 1231 formed on the bottom of the housing 120, 130, 140, and is compressed and lifted in the upward direction by the fan.

A substrate mounting unit 1331 for the UV LED substrate 150 is disposed on the fan mounting unit 132, and a photocatalytic filter mounting unit 1332 having the photocatalytic filter 180 mounted thereon is disposed above the substrate mounting unit 1331 to be separated therefrom by a predetermined distance The UV LED substrate 150 mounted on the substrate mounting unit 1331 has a slim, elongated plate shape and includes a UV LED 151 mounted on an upper surface thereof. The UV LED substrate may be provided in plural depending upon the number of UV LEDs corresponding to the size of the air cleaner. In this embodiment, the air cleaner includes two substrates.

The irradiation angle and wavelength of the UV LED, the shape and direction of the photocatalytic filter, the distance between the UV LED and the photocatalytic filter, and a relationship between the direction of UV light and the flow direction of air have already described in the above embodiment, and a repeated description is omitted herein.

As shown in the drawings, in the inner housing, an inner side surface of the photocatalytic filter mounting unit 1332 has a shape corresponding to the shape of an outer side surface of the photocatalytic filter, and a lower end of the photocatalytic filter mounting unit 1332 has a stepped portion. Accordingly, the photocatalytic filter 180 may be mounted on the photocatalytic filter mounting unit by placing the photocatalytic filter 80 thereon from above the inner housing.

On the other hand, in the outer housing, the upper housing 140 is detachably coupled to an upper surface of the body housing 120. Accordingly, when the upper housing 140 is separated from the body housing 120, an opening is formed at a portion of the body housing 120 such that the photocatalytic filter can be inserted into or removed from the body housing 120 therethrough.

The base housing 110 is connected to the lower end of the housing 120, 130, 140, which receives various components for purification of air, and separates the bottom surface of the housing from the floor on which the air cleaner is placed.

The base housing 110 may include a neck member 111 connected to a central portion of the lower housing 123 and a lower member 112 connected to a lower end of the neck member 111. The neck member 111 has a streamlined shape gradually widening from an upper end thereof connected to the lower housing to the lower end thereof to guide the flow of air introduced through the suction port 1231 formed on the lower housing 123. The suction port 1231 is formed around the central portion of the lower housing 123 to act as a passage through which air flows.

In this embodiment, the base housing 110 is secured to a central portion of the bottom of the body housing 120 to support the body housing. Here, the weight of the body housing is concentrated on the central portion of the lower housing 123. Thus, the lower housing 123 is required to have sufficient strength to endure the weight of the body housing. However, as described above, since the suction port 1231 is formed on the lower housing 123, strength of the lower housing 123 is inevitably weakened.

Thus, according to this embodiment, the lower housing 123 is provided with a plurality of ribs 1232, which radially extend from the central portion of the lower housing to an outer periphery thereof, in order to reinforce the lower housing 123. Furthermore, an arc-shaped grate 1233 is disposed between the ribs 1232 and connects the ribs 1232 to each other to reinforce the ribs. Accordingly, the grate 1233 provides not only a function of blocking foreign matter from entering the air cleaner but also a function of reinforcing the lower housing 123.

According to this embodiment, electric/electronic components are very efficiently arranged in the air cleaner. Not only does the base housing 110 act to support the housing 120, 130, 140, but also provides a useful installation space. A space between the neck member 111 and the lower member 112 constituting the base housing 110 is provided with a control PCB 113 for controlling operation of each component of the air cleaner. A connector 114 is disposed at a rear side of the control PCB 113 and is connected to an external power source.

Power supplied through the connector is supplied to the fan 160 and the UV LED substrate 150 in the inner housing. In addition, the power source is connected to a display unit 211, 212, 213 mounted on the side housing 121 and a handling unit 141, 142, 143 mounted on the upper housing 140. Connection lines extend into the housing through a connection portion between the neck member 111 and the lower housing 123 communicating with each other.

The display unit includes a fastening portion 1211 formed on an inner surface of the side housing 121, a display PCB 1212 fastened to the fastening portion 1211, and a display screen 213 disposed on the front housing to be adjacent to the display PCB to display operation of the air cleaner through on/off and colors of a light emitting diode provided to the display PCB.

The handling unit is disposed near the display unit, and includes a fastening portion 141 formed on a lower surface of the upper housing 140, a handling PCB 42 fastened to the fastening portion 41, and the button 143 disposed on the front region of the upper housing 40.

Accordingly, power lines connected to the two PCBs 1212, 142 can be disposed along the inner surface of the side housing.

Although this embodiment is a modification of the air cleaner shown in FIG. 3 formed by changing the locations of the fan and the photocatalytic module (photocatalytic filter and UV light source) (see FIG. 7), it should be understood that such a modification can also be applied not only to the air cleaner of FIG. 3, but also to the air cleaner shown in FIG. 5 or FIG. 9.

Although some embodiments have been described herein with reference to the accompanying drawings, it should be understood that these embodiments and the drawings are provided for illustration only and are not to be construed in any way as limiting the invention, and that various modifications, changes, and alterations can be made by those skilled in the art without departing from the spirit and scope of the invention. In addition, it should be understood that other advantageous effects not described in the above description of the invention and apparent therefrom also fall within the scope of the invention.

The invention claimed is:

1. An air cleaner comprising:
   an outer housing formed with a suction port and a discharge port;
   an inner housing disposed inside the outer housing and separated from the outer housing by a substantially cylindrical gap between an outer surface of the inner housing and an inner surface of the outer housing, wherein the inner housing is configured to receive air that passes through the substantially cylindrical gap from the suction port of the outer housing;
   a fan disposed in the inner housing and inducing a discharge of air towards the discharge port;
   a photocatalytic filter disposed in the inner housing in an air discharge direction from the fan or in an opposite direction to the air discharge direction;
   a UV light source disposed before the photocatalytic filter in a direction of air flow entering from the suction port and passing through the fan and emitting UV light towards the photocatalytic filter; and a collection filter disposed in the inner housing and arranged at a position before the fan, the photocatalytic filter and the UV light source in the direction of the air flow.

2. The air cleaner according to claim 1, further comprising:

a sensor disposed on the outer surface of the inner housing or the inner surface of the outer housing to measure a quality of air flowing in the substantially cylindrical gap.

3. The air cleaner according to claim 1, wherein the fan pushes air in an upward direction and the photocatalytic filter is located in an upper portion of the inner housing.

4. The air cleaner according to claim 1, wherein a distance between the UV light source and the photocatalytic filter ranges from 25 mm to 40 mm.

5. The air cleaner according to claim 1, wherein the collection filter comprises a HEPA filter having a cylindrical an outer peripheral surface.

6. The air cleaner according to claim 5, wherein the collection filter further comprises a carbon filter disposed on the outer peripheral surface of the HEPA filter, the carbon filter having a cylindrical shape corresponding to a shape of the HEPA filter and a larger size than the HEPA filter.

7. The air cleaner according to claim 1, wherein the collection filter has a cylindrical shape and comprises a filter member disposed on an outer peripheral surface thereof, wherein the discharge port is formed on an upper side of the outer housing and the suction port is formed at a lower portion of a side surface of the outer housing, and wherein the collection filter is fitted into the air cleaner in a horizontal direction such that a lower surface of the collection filter is brought into close contact with a bottom of the outer housing and an upper surface of the collection filter is brought into close contact with a lower surface of a fan installation unit of the inner housing.

8. The air cleaner according to claim 7, wherein the outer housing comprises a bottom housing comprising an upper member and a lower member that are separated from each other by a predetermined distance, the lower surface of the collection filter being brought into close contact with an upper surface of the upper member, and a control PCB controlling operation of the air cleaner comprising a connector connected to an exterior power source is disposed in a space between the upper member and the lower member.

9. The air cleaner according to claim 7, wherein the outer housing comprises a body housing defining a side surface thereof, a body housing comprising a front housing and a rear housing, the rear housing being detachably coupled to the outer housing such that the collection filter can be inserted into and removed from the air cleaner through an opening formed by separation of the rear housing.

10. The air cleaner according to claim 1, wherein the outer housing comprises an upper housing defining an upper surface thereof and the upper housing provided with a handling unit.

11. An air cleaner comprising:

a housing having a suction port and a discharge port;

a fan disposed in the housing and inducing a discharge of air towards the discharge port;

a photocatalytic filter disposed in the housing in an air discharge direction from the fan or in an opposite direction to the air discharge direction; and a light source disposed before the photocatalytic filter in a direction of air flow entering from the suction port and passing through the fan and emitting light to the photocatalytic filter, and wherein the housing includes an inner housing in which the fan, the light source, and the photocatalytic filter are disposed, wherein the inner housing is separated from the housing by a gap, and wherein the inner housing is configured to receive air that passes through the gap from the suction port of the housing.

12. The air cleaner according to claim 11, wherein the housing comprises:

an outer housing having the suction port formed on a bottom surface thereof and the discharge port formed on an upper surface thereof.

13. The air cleaner according to claim 12, wherein the fan pushes air in an upward direction and the photocatalytic filter is located in an upper portion of the inner housing.

14. The air cleaner according to claim 13, wherein the outer housing comprises an upper housing comprising an upper surface having the discharge port formed thereon, and the upper housing is detachably coupled to the outer housing such that the photocatalytic filter can be inserted into and removed from the air cleaner through an opening formed by separation of the upper housing.

15. The air cleaner according to claim 11, wherein the housing further includes a base housing disposed under the housing and supporting the housing such that a lower surface of the housing is separated from a bottom of the base housing.

16. The air cleaner according to claim 15, wherein the base housing comprises:

a neck member connected to a central portion of a lower side of the housing and having a width gradually increasing towards a lower end thereof; and a lower member formed at the lower side of the neck member, wherein the neck member is communicated with an interior space of the housing through an upper side thereof, wherein a control PCB controls operation of the air cleaner and includes a connector connected to an exterior power source, and wherein the control PCB is disposed in a space between the neck member and the lower member.

17. The air cleaner according to claim 15, wherein the base housing comprises a neck member connected to a central portion of a lower side of the housing and having a width gradually increasing towards a lower end thereof; the housing comprises a lower housing constituting a lower portion thereof, an upper end of the neck member being secured to a central portion of the lower housing; and the suction port is formed along an outer circumference of the central portion of the lower housing.

18. The air cleaner according to claim 11, wherein the housing comprises an outer housing having the suction port and the discharge port.

19. The air cleaner according to claim 18, wherein the inner housing comprises a fan housing receiving the fan, and a photocatalyst housing receiving the photocatalytic filter and the light source, wherein the fan housing is disposed on the mounting unit, and wherein the photocatalyst housing is disposed on the fan housing.

20. The air cleaner according to claim 11, wherein the housing comprises an upper housing defining an upper surface thereof and the upper housing has a patterned shape.

21. The air cleaner according to claim 1, wherein air passes in through the suction port, then across the gap, then through the collection filter, then to the interior of the inner housing, then out the discharge port.

* * * * *